(12) United States Patent
Genta et al.

(10) Patent No.: US 9,315,840 B2
(45) Date of Patent: Apr. 19, 2016

(54) BIOMASS PROCESSING SYSTEM, SACCHARIDE SOLUTION PRODUCTION METHOD USING BIOMASS FEEDSTOCK, ALCOHOL PRODUCTION METHOD

(75) Inventors: Minoru Genta, Tokyo (JP); Seiichi Terakura, Tokyo (JP); Hideo Suzuki, Tokyo (JP); Yoshio Kuromi, Tokyo (JP); Yoshitaka Kimura, Tokyo (JP)

(73) Assignee: MITSUBISHI HEAVY INDUSTRIES MECHATRONICS SYSTEMS, LTD., Kobe-shi (JP)

( * ) Notice: Subject to any disclaimer, the term of this patent is extended or adjusted under 35 U.S.C. 154(b) by 0 days.

(21) Appl. No.: 14/381,511

(22) PCT Filed: Mar. 29, 2012

(86) PCT No.: PCT/JP2012/058460
§ 371 (c)(1),
(2), (4) Date: Aug. 27, 2014

(87) PCT Pub. No.: WO2013/145236
PCT Pub. Date: Mar. 10, 2013

(65) Prior Publication Data
US 2015/0044729 A1    Feb. 12, 2015

(51) Int. Cl.
*B01D 36/00* (2006.01)
*B01D 61/20* (2006.01)
(Continued)

(52) U.S. Cl.
CPC . *C12P 19/14* (2013.01); *B09B 3/00* (2013.01); *C08H 8/00* (2013.01); *C12M 21/12* (2013.01);
(Continued)

(58) Field of Classification Search
CPC ...... B01D 21/00; B01D 21/009; B01D 17/00; B01D 36/00; B01D 36/003; B01D 36/008; B01D 36/04; B01D 37/00; B01D 61/14; B01D 61/16; B01D 61/20; B01D 2311/04; B01D 2311/06; B01D 2311/08; B01D 2311/25; B01D 2311/26; B01D 2311/2646; B01D 2311/2688; B01D 2311/2623; C02F 9/00; C02F 2103/28; B01J 3/00; B01J 3/02; B01J 3/006; B01J 4/00; B01J 4/001; C12P 7/02; C12P 7/08; C12P 7/10; C12P 19/02; C12P 19/14; C12P 19/00; C08H 8/00; C12M 21/12; C12M 21/18; C12M 45/02; C12M 45/04; C12M 45/20; C12M 27/00; C12M 45/06; C12M 47/10; C12M 1/005; C12M 1/12; C12M 1/26; C12M 1/28; C12M 1/36; C12M 1/38; C12M 21/00; C12M 41/12; C12M 41/14; C12M 41/16; C12M 41/18; C12M 43/00; C12M 47/12; C12M 47/20; Y02E 50/10; Y02E 50/16
USPC .............. 210/632, 749, 774, 804–806, 808; 127/23, 24, 27, 37, 1; 44/307, 605, 44/606; 435/161–165; 568/840, 913, 914
See application file for complete search history.

(56) References Cited

U.S. PATENT DOCUMENTS 4,023,982 A * 5/1977 Knauth ............................ 127/1
4,650,689 A * 3/1987 Hedrick ........................ 426/600
(Continued)

FOREIGN PATENT DOCUMENTS

CA      2 750 754 A1    1/2012
JP      9-507386 A      7/1997
(Continued)

OTHER PUBLICATIONS

Decision of a Patent Grant dated Nov. 12, 2013, issued in Application No. 2013-536355, w/English translation. (4 pages).
(Continued)

*Primary Examiner* — Joseph Drodge
(74) *Attorney, Agent, or Firm* — Westerman, Hattori, Daniels & Adrian, LLP

(57) ABSTRACT

A biomass processing system includes: a hydrolysis processing unit that decomposes, under a high-temperature/high-pressure condition, biomass feedstock in a processing tank having a gas-liquid interface, and removes a lignin component and a hemicellulose component; a biomass solid content discharge unit that discharges a biomass solid content 20 which is a hot water insoluble element; a slurrying vessel that subjects the discharged biomass solid content to slurrying; and a hot water discharge liquid introducing line L2 that introduces, into the slurrying vessel 21, a hot water discharge liquid 16 including a biomass hot-water soluble element.

7 Claims, 7 Drawing Sheets

(51) Int. Cl.

| | | |
|---|---|---|
| C12P 19/02 | (2006.01) | |
| C12P 19/14 | (2006.01) | |
| C12M 1/12 | (2006.01) | |
| C12M 1/38 | (2006.01) | |
| C12M 1/26 | (2006.01) | |
| B09B 3/00 | (2006.01) | |
| C12P 7/10 | (2006.01) | |
| C08H 8/00 | (2010.01) | |
| C13K 1/02 | (2006.01) | |
| C12M 1/40 | (2006.01) | |
| C12M 1/02 | (2006.01) | |
| C12M 1/00 | (2006.01) | |
| C12P 7/02 | (2006.01) | |
| C12M 1/33 | (2006.01) | |

(52) U.S. Cl.
CPC ............... *C12M 21/18* (2013.01); *C12M 27/00* (2013.01); *C12M 45/02* (2013.01); *C12M 45/04* (2013.01); *C12M 45/20* (2013.01); *C12M 47/10* (2013.01); *C12P 7/02* (2013.01); *C12P 7/10* (2013.01); *C12P 19/02* (2013.01); *C13K 1/02* (2013.01); *C12P 2201/00* (2013.01); *C12P 2203/00* (2013.01); *Y02E 50/16* (2013.01)

(56) References Cited

U.S. PATENT DOCUMENTS

| | | | |
|---|---|---|---|
| 4,859,322 A | | 8/1989 | Huber |
| 5,348,871 A | * | 9/1994 | Scott et al. .................... 435/165 |
| 5,424,417 A | * | 6/1995 | Torget et al. .................... 536/56 |
| 8,123,864 B2 | * | 2/2012 | Christensen et al. ............ 127/37 |
| 8,163,517 B2 | * | 4/2012 | Genta et al. .................... 435/41 |
| 8,728,770 B2 | * | 5/2014 | Ishikawa .................. C12P 19/02 435/100 |
| 9,102,956 B2 | | 8/2015 | Genta et al. |
| 2007/0259412 A1 | * | 11/2007 | Belanger et al. .............. 435/161 |
| 2008/0026431 A1 | | 1/2008 | Saito et al. |
| 2008/0299628 A1 | * | 12/2008 | Hallberg et al. .............. 435/139 |
| 2010/0108567 A1 | * | 5/2010 | Medoff .......................... 208/49 |
| 2010/0269990 A1 | * | 10/2010 | Dottori et al. .................... 162/21 |
| 2010/0317843 A1 | * | 12/2010 | Sudhakaran ............. D21C 3/02 536/56 |
| 2010/0330638 A1 | | 12/2010 | Aita et al. |
| 2011/0003348 A1 | | 1/2011 | Genta et al. |
| 2011/0079219 A1 | * | 4/2011 | McDonald et al. ................. 127/1 |
| 2012/0006320 A1 | * | 1/2012 | Nguyen .......................... 127/34 |
| 2012/0009642 A1 | | 1/2012 | Suzuki et al. |
| 2012/0315683 A1 | | 12/2012 | Mosier et al. |
| 2013/0122555 A1 | | 5/2013 | Suzuki et al. |
| 2014/0004571 A1 | * | 1/2014 | Garrett et al. .................... 435/99 |
| 2014/0273127 A1 | * | 9/2014 | Fuchs et al. .................... 435/160 |

FOREIGN PATENT DOCUMENTS

| | | |
|---|---|---|
| JP | 11-506934 A | 6/1999 |
| JP | 2003-311141 A | 11/2003 |
| JP | 2004-105855 A | 4/2004 |
| JP | 2005-168335 A | 6/2005 |
| JP | 2006-136263 A | 6/2006 |
| JP | 2009-183153 A | 8/2009 |
| JP | 2009-183154 A | 8/2009 |
| JP | 2009-183805 A | 8/2009 |
| JP | 4764527 B1 | 9/2011 |
| JP | 4764528 B1 | 9/2011 |
| WO | 2009/096061 A1 | 8/2009 |
| WO | 2013/082616 A2 | 6/2013 |

OTHER PUBLICATIONS

International Search Report dated Jul. 3, 2012 issued in corresponding application No. PCT/JP2012/058460.
Written Opinion of the International Searching Authority dated Jul. 3, 2012 issued in corresponding application No. PCT/JP2012/058460.
Office Action dated Mar. 19, 2015, issued in U.S. Appl. No. 13/121,969 (21 pages).
Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
Notice of Allowance dated Aug. 19, 2015, issued in co-pending U.S. Appl. No. 12/438,792 (12 pages).
Notice of Allowance dated Aug. 12, 2015, issued in co-pending U.S. Appl. No. 13/578,116 (48 pages).
Notice of Allowance dated Jul. 6, 2015, issued in Indonesian application No. W-00201103522 (w/ English translation) (4 pages).
English translation of Written Opinion of the International Searching Authority dated Jul. 3, 2012, issued in counterpart international application No. PCT/JP2012/058460 (4 pages).
Office Action dated Jul. 10, 2015, issued in counterpart Australian Patent No. 2012374915, counterpart to co-pending U.S. Appl. No. 13/700,753 (5 pages).
Notice of allowance dated Sep. 30, 2015 issued in Canadian application No. 2,791,665 counterpart to U.S. Appl. No. 13/578,116 (in English) (1 page).
Decision of a Patent Grant dated Nov. 10, 2015 issued in Japan application No. 2010-154233 counterpart to U.S. Appl. No. 13/700,759 (w/ English translation) (5 pages).
Non-Final Office Action dated Sep. 25, 2015, issued in co-pending U.S. Appl. No. 13/132,034 (39 pages).
Final Office Action dated Sep. 28, 2015, issued in co-pending U.S. Appl. No. 13/203,848 (34 pages).

* cited by examiner

BIOMASS PROCESSING SYSTEM, SACCHARIDE SOLUTION PRODUCTION METHOD USING BIOMASS FEEDSTOCK, ALCOHOL PRODUCTION METHOD

FIELD

The present invention relates to a biomass processing system capable of efficiently decomposing biomass feedstock, a saccharide solution production method using biomass feedstock, and an alcohol production method.

BACKGROUND

In the related art, there has been put into practice a technique of producing ethanol and the like, in which biomass such as wood is subjected to saccharification processing using dilute sulfuric acid and concentrated sulfuric acid and then subjected to solid-liquid separation, and a liquid phase is neutralized to be utilized as feedstock for ethanol fermentation and the like (Patent Literature 1, Patent Literature 2).

Furthermore, chemical industrial material production (for example, lactic acid fermentation) using saccharide as starting feedstock may also be considered.

Here, the biomass refers to organisms incorporated into the substance circulation system of the earth biosphere, or accumulation of organic materials derived from the organisms (see JIS K 3600 1258).

Here, sugar cane, corn, and the like currently used as alcohol material are originally provided as food, and it is not preferable to use such edible resources as industrial application resources for a long period of time in a stable manner from the perspective of life cycles of useful foodstuffs.

For this reason, it is an important problem to effectively make use of cellulose resources such as herbaceous biomass and woody biomass which are considered to be useful resources in the future.

Furthermore, in the cellulose resources, cellulose is 38 to 50%, and a hemicellulose component is 23 to 32%, which vary, and a lignin component not serving as fermentation feedstock is 15 to 22%, which also varies. Since this is an industrialization study involving many problems, feedstock is considered in a fixed manner, and currently, there has not yet been made any disclosure of a technique of a production system based on consideration of the versatility of feedstock.

Further, originally an aim is considered to cope with waste problem and prevent global warming using feedstock which is more disadvantageous for fermentation feedstock than starch feedstock, and therefore, a production system based on a fixed notion of feedstock is less meaningful. The production system needs to be applicable to a wide range of wastes in general. Currently, an enzymatic saccharification method itself has too low efficiency and is regarded as a future problem. The saccharification rate by acid treatment is a very small value on the order of about 75% (based on components that can be saccharified) because of excessive decomposition of saccharide due to overreaction. Therefore, for the cellulose resources, the ethanol production yield stays at about 25% (Patent Literature 3).

It is noted that in the techniques in the related art of Patent Literatures 1 to 3, side-reaction products have caused enzymatic saccharification inhibition, and there occurs a phenomenon that the saccharide yield decreases, and therefore, a hydrolysis apparatus that removes an enzymatic saccharification inhibition substance and enhances enzymatic saccharification performance for mainly cellulose has been proposed previously (Patent Literatures 4 to 7).

CITATION LIST

Patent Literature

Patent Literature 1: Japanese PCT National Publication No. H9-507386
Patent Literature 2: Japanese PCT National Publication No. H11-506934
Patent Literature 3: Japanese Patent Laid-open No. 2005-168335
Patent Literature 4: Japanese Patent Laid-open No. 2009-183805
Patent Literature 5: Japanese Patent Laid-open No. 2009-183154
Patent Literature 6: Japanese Patent No. 4764527
Patent Literature 7: Japanese Patent No. 4764528

SUMMARY

Technical Problem

In the proposition of the hydrolysis apparatus in the Patent Literature 6 mentioned above, water is provided from the outside when slurrying is performed in a slurrying vessel 1, and therefore, the water usage amount in the entire plant increases, and there is such a problem that the cost effectiveness of the plant deteriorates.

In the proposition of the hydrolysis apparatus in the Patent Literature 7 mentioned above, a slurry biomass solid content subjected to slurrying in a slurrying vessel and a hot water discharge liquid are saccharified in different lines, and therefore, the line needs to be of two systems, and there is such a problem that the plant equipment becomes complex and also the cost effectiveness deteriorates.

The present invention is made in view of the above problems, and provides a biomass processing system having improved plant efficiency, a saccharide solution production method using biomass feedstock, and an alcohol production method.

Solution to Problem

According to a first aspect of the present invention in order to solve the above problems, there is provided a biomass processing system including: a hydrolysis processing unit that decomposes, under a high-temperature/high-pressure condition, biomass feedstock including cellulose, hemicellulose, and lignin in a processing tank having a gas-liquid interface, and removes a lignin component and a hemicellulose component; a biomass solid content discharge unit that discharges the biomass solid content which is a hot water insoluble element processed by the hydrolysis processing unit; a slurrying vessel that is in communication with the biomass solid content discharge unit and that subjects the discharged biomass solid content to slurrying; and a discharge liquid introducing line that introduces, into the slurrying vessel, a hot water discharge liquid including a biomass hot-water soluble element discharged from the hydrolysis processing unit, wherein the biomass solid content is mixed with the discharge liquid to be made into mixture slurry.

According to a second aspect of the present invention, there is provided the biomass processing system according to the first aspect, wherein a filter is interposed on the discharge liquid introducing line.

According to a third aspect of the present invention, there is provided the biomass processing system according to the first or second aspect, wherein cooling means is interposed on the discharge liquid introducing line.

According to a fourth aspect of the present invention, there is provided the biomass processing system according to any one of the first to third aspects, including a saccharification tank that saccharifies the mixture slurry subjected to the slurrying in the slurrying vessel.

According to a fifth aspect of the present invention, there is provided the biomass processing system according to the fourth aspect, including: a solid-liquid separation device that separates a solid element from a saccharide solution saccharified by the saccharification tank; and a moisture separation device that removes water from the saccharide solution from which the solid element has been separated.

According to a sixth aspect of the present invention, there is provided the biomass processing system according to the fifth aspect, including a water return line that returns water separated from the moisture separation device back to the slurrying vessel.

According to a seventh aspect of the present invention, there is provided the biomass processing system according to the sixth aspect, including an organism processing apparatus in the water return line.

According to an eighth aspect of the present invention, there is provided a saccharide solution production method using biomass feedstock, including: providing the biomass feedstock including cellulose, hemicellulose, and lignin from a normal pressure state to a pressurized state, and performing hydrolysis processing by a hydrolysis processing unit on the biomass feedstock under a high-temperature/high-pressure condition; and subsequently, charging a biomass solid content discharged from the biomass processing unit into a slurrying vessel into which water has been poured and which is in communication with the biomass processing unit, and making the biomass solid content into a slurry biomass solid content; and subjecting the slurry biomass solid content to enzymatic saccharification to obtain a saccharide solution, thereafter separating a solid content, and then removing water, wherein a hot water discharge liquid including a biomass hot-water soluble element discharged from the hydrolysis processing unit is charged into the slurrying vessel and subjected to slurrying to be made into a mixture slurry.

According to a ninth aspect of the present invention, there is provided the saccharide solution production method using biomass feedstock according to the eighth aspect, wherein impurity in the discharge liquid discharged from the hydrolysis processing unit is removed.

According to a tenth aspect of the present invention, there is provided an alcohol production method, wherein a saccharide solution obtained by a saccharide solution production method using biomass feedstock is used to perform alcohol fermentation and alcohol is produced. As another aspect, a saccharide solution production method using biomass feedstock comprises:

providing the biomass feedstock including cellulose, hemicellulose, and lignin from a normal pressure sate to a pressurized state, and performing hydrolysis processing by a hydrolysis processing unit on the biomass feedstock under a high-temperature/high-pressure condition, and
subsequently, charging a biomass solid content discharged from the biomass processing unit into a slurrying vessel into which water has been poured and which is in communication with the biomass processing unit, and making the biomass solid content into a slurry biomass solid content, and
subjecting the slurry biomass solid content to enzymatic saccharification to obtain a saccharide solution, thereafter separating a solid content, and then removing water,
wherein a hot water discharge liquid including a biomass hot-water soluble element discharged from the hydrolysis processing unit is charged into the slurrying vessel and subjected to slurrying to be made into a mixture slurry, As still another aspect, in the saccharide solution production method using biomass feedstock, impurity in the discharge liquid discharged from the hydrolysis processing unit is removed.

Advantageous Effects of Invention

According to the present invention, the amount of water introduced when slurrying processing is performed is greatly reduced, and therefore the plant efficiency can be improved.

DESCRIPTION OF EMBODIMENTS

Preferred embodiments of a biomass processing system according to the present invention will be hereinafter explained in detail with reference to appended drawings. It is noted that the present invention is not limited by the embodiments, and when there are multiple embodiments, an embodiment including a combination of the embodiments is also included.

First Embodiment

A biomass processing system according to the present invention will be explained with reference to drawings.

Figure 1:
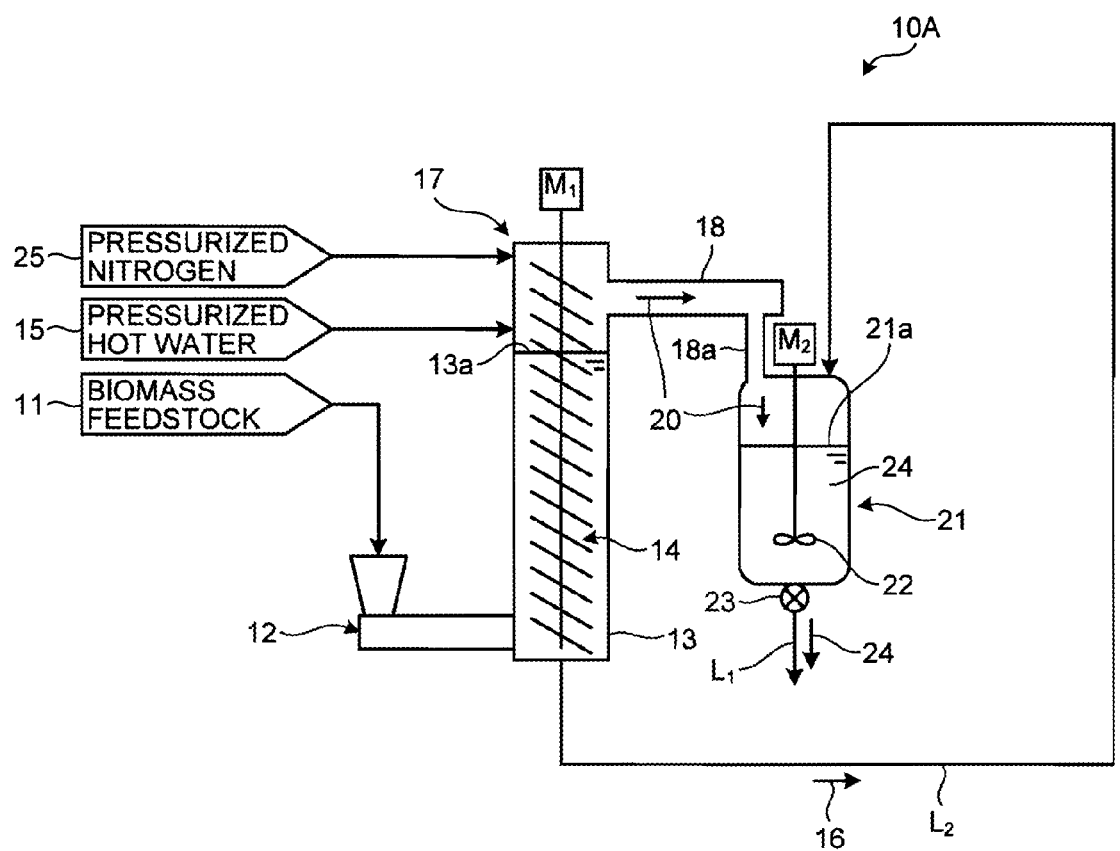
FIG. 1 is a schematic diagram of a biomass processing system according to a first embodiment.

FIG. 1 is a schematic diagram of the biomass processing system according to the first embodiment.

As illustrated in FIG. 1, a biomass processing system 10A according to the present embodiment includes a hydrolysis processing unit 17 which is a biomass processing unit that decomposes cellulose, hemicellulose, and lignin from biomass feedstock 11 under a high-temperature/high-pressure condition in an apparatus main body 13 which is a processing tank having a gas-liquid interface 13a and that removes a lignin component and a hemicellulose component, a biomass solid content discharge unit 18 that discharges a biomass solid content 20 which is a hot water insoluble element processed by the hydrolysis processing unit 17, a slurrying vessel 21 that is in communication with the biomass solid content discharge unit 18 and that subjects a biomass solid content to slurrying by introducing the discharged biomass solid content 20, a discharge unit 23 that discharges the slurry biomass solid content from a pressurized state to a normal pressure state, and a hot water discharge liquid introducing line $L_2$ that introduces, into the slurrying vessel 21, a hot water discharge liquid 16 including a biomass hot-water soluble element discharged from the hydrolysis processing unit 17.

The hydrolysis processing unit 17 includes a biomass providing unit 12 that provides the biomass feedstock 11 including cellulose, hemicellulose, and lignin from the normal pressure state to the pressurized state.

Then, in the hydrolysis processing unit 17, the provided biomass feedstock 11 is conveyed from the lower side to the upper side by first screw means 14 serving as conveying means inside the apparatus main body 13, and also pressurized hot water (which may be hereinafter also referred to as "hot water") 15 is provided into the apparatus main body 13 from the upper side different from a portion where the biomass feedstock 11 is provided, the biomass feedstock 11 and the pressurized hot water 15 are subjected to hydrolysis while being brought into countercurrent contact, a hot water dissolved component (a soluble element such as a lignin component and a hemicellulose component) is transferred into the hot water discharge liquid 16 which is pressurized hot water to be discharged, and the lignin component, the hemicellulose component, and the like are separated from the biomass feedstock 11.

Here, the screw means is exemplified as the conveying means in the present embodiment; however, the conveying means is not limited to the screw means as long as it can convey the biomass solid content from the lower side to the upper side.

The discharge liquid 16 including the biomass hot-water soluble element is introduced into the slurrying vessel 21, so that this can eliminate the necessity of water 19, which is required in the slurrying vessel 21 and is charged from the outside.

Figure 2:
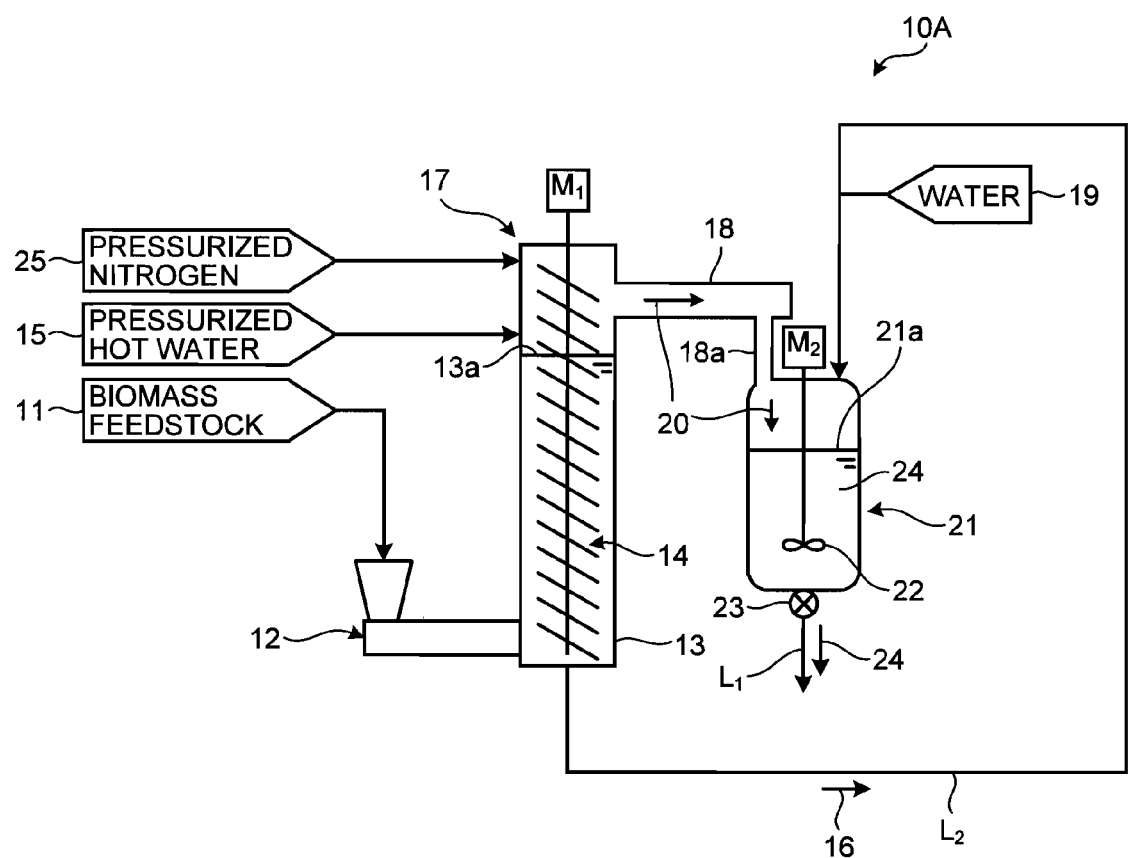
FIG. 2 is a schematic diagram of the biomass processing system according to the first embodiment.

It is noted that when water is required in slurrying, a minimum required amount of the water 19 may be introduced from the outside as illustrated in FIG. 2.

In order to suppress excessive decomposition (a decomposition start temperature of about 140° C. to 180° C.) of hemicellulose included in the moisture contained in the biomass solid content 20, the temperature of the discharge liquid 16 to be introduced according to the temperature of the biomass solid content 20 or the capacity of the slurrying vessel 21 may be set appropriately by cooling with not-illustrated cooling means, as necessary, so that the liquid temperature of the slurrying vessel 21 is cooled to 140° C. or less.

In the present embodiment, the biomass solid content 20 which is the hot water insoluble element that becomes a hexose feedstock is dropped into the discharge liquid 16 including the biomass hot-water soluble element that becomes pentose feedstock, to be made into mixture slurry 24. Thus, a saccharification step can be achieved in a single line.

Here, in FIG. 1, reference character 18a denotes a passage communicating between the biomass solid content discharge unit 18 and the slurrying vessel 21, reference character 22 denotes agitation means that agitates the inside of the slurrying vessel 21, reference character 13a denotes a gas-liquid interface of the apparatus main body 13, reference character 21a denotes a gas-liquid interface of the slurrying vessel 21, reference character $L_1$ denotes a discharge line of the mixture slurry 24, reference character $M_1$ denotes a motor that drives the first screw means 14, and reference character $M_2$ denotes a motor that drives the agitation means 22.

In FIG. 1, the biomass solid content discharge unit 18 is provided with not-illustrated second screw means, and the biomass solid content 20 which is the hot water insoluble element conveyed from the lower side to the upper side by the first screw means 14 is being discharged to the slurrying vessel 21 side. Then, the discharged biomass solid content 20 sequentially drops from the passage 18a into the hot water discharge liquid 16, and is subjected to slurrying by agitation of the agitation means 22 provided within the slurrying vessel 21, and made into the mixture slurry 24.

Furthermore, the biomass solid content 20 dropped into the liquid in the slurrying vessel 21 is cooled by direct thermal exchange with the liquid, and as a result, excessive decomposition of the remaining hemicellulose, the remaining lignin, and the main component cellulose due to the hot water accompanied by the biomass solid content 20 is suppressed.

This is because in the gas atmosphere at the upper side of the gas-liquid interface 13a of the hydrolysis processing unit 17, the biomass solid content 20 is exposed above the hot water liquid surface (gas-liquid interface 13a) by the first screw means 14. However, due to the existence of the pressurized hot water 15 accompanied by the biomass solid content 20, the reaction still proceeds in the high-temperature/high-pressure state, and therefore, the reaction can be stopped by charging the biomass solid content 20 into the liquid in the slurrying vessel 21.

Therefore, this reaction stoppage suppresses the excessive decomposition of the remaining hemicellulose, the remaining lignin, and the main component cellulose, and while the excessive decomposition of the cellulose component is suppressed and the recovery rate thereof is improved, generation of a reaction inhibition component in the downstream side is suppressed.

In addition, since the slurry liquid exists in the slurrying vessel 21, the liquid sealing is made at the gas-liquid interface 13a of the hydrolysis processing unit 17 and the gas-liquid interface 21a of the slurrying vessel 21, and this prevents leakage of pressurized nitrogen 25 which is gas for pressurization. Thus, the loss associated with the gas leakage is eliminated, and the running cost for the gas for pressurization can be greatly reduced. It is noted that in the slurrying vessel 21, there are provided a safety valve and an inlet passage of the pressurized nitrogen 25, which are not illustrated.

In addition, the biomass solid content 20 is subjected to the slurrying with the discharge liquid 16 including the biomass hot-water soluble element, whereby fluidization becomes possible, and a discharge mechanism used in discharging to the outside from the slurrying vessel 21 become simple. In other words, if the biomass solid content 20 is still at a high-temperature state, the material of the discharge mechanism also needs to be, for example, an expensive material, but since the biomass solid content is cooled in the slurrying vessel 21, for the material of the discharge unit 23 provided at the discharge side thereof, inexpensive stainless, resin, or the like can be used. As this discharge unit 23, for example, a rotary feeder, a flow regulating valve, or the like can be used.

In addition, although the biomass solid content 20 has a high void ratio and a low bulk density and thus the handling in the solid state has been troublesome, the volume reduction can be achieved by slurrying, and the handling also becomes easy.

In other words, before the biomass solid content 20 is added to the liquid, the biomass solid content 20 is in a so-called cake form, and has a high rate of the gas for pressurization, a high void ratio, and a bulk density as low as 0.5 g/cc or less. However, when the biomass solid content 20 is subjected to slurrying, the void ratio decreases, and the volume reduction can be achieved.

Further, the biomass solid content 20 is subjected to the slurrying with the discharge liquid 16 including the biomass hot-water soluble element, whereby fluidization becomes possible, and the handling in the subsequent saccharification step becomes easy.

In particular, in the saccharification processing and the like, it is necessary to cool to a predetermined temperature or less (for example, 60° C. or less) because there is enzyme reaction. In this case, cooling in the state of the biomass solid content 20 is not favorable in terms of the heat exchange efficiency thereof, and therefore, large scale heat exchange means is required, but by subjecting the biomass solid content 20 to slurrying, the cooling efficiency becomes favorable, and the large scale heat exchange means becomes unnecessary.

Furthermore, indirect cooling means for cooling the inside of the slurrying vessel 21 may be provided.

Furthermore, although the slurrying vessel 21 is provided with the agitation means 22, the present invention is not limited thereto, and for example, the agitation can be carried out by using circulation means with a pump.

Here, the biomass provided to the hydrolysis processing unit 17 is not particularly limited, and refers to organisms incorporated into the substance circulation system of the earth biosphere, or accumulation of organic materials derived from the organisms (see JIS K 3600 1258), but in the present invention, in particular, cellulose resources such as woody, for example, hardwood resources and herbaceous resources, and agricultural waste, food waste, and the like are preferably used.

Furthermore, as for the biomass feedstock 11, the particle diameter is not particularly limited, but the biomass feedstock 11 is preferably milled to 5 mm or less.

In the present embodiment, before the biomass is provided, for example, preprocessing may be performed by using a mill as a preprocessing apparatus. Furthermore, washing may be performed by a washing apparatus.

It is noted that when the biomass feedstock 11 is, for example, hulls and the like, the biomass feedstock 11 can be provided to the biomass providing unit 12 directly without milling.

Furthermore, the reaction temperature in the hydrolysis processing unit 17 is preferably in the range of 180 to 240° C. More preferably, the reaction temperature is 200 to 230° C.

This is because at a low temperature of less than 180° C., the hydrolysis speed is low, and it takes a long time for decomposition, leading to increasing in size of an apparatus, which is not preferable. On the other hand, at a temperature of more than 240° C., the decomposition speed is too high, and the cellulose component changes from the solid state to the liquid state more greatly, and also the excessive decomposition of hemicellulose saccharide is promoted, which is not preferable.

Furthermore, the hemicellulose component begins to dissolve from about 140° C., the cellulose begins to dissolve from about 230° C., and the lignin component begins to dissolve from about 140° C.; however, the range of 180° C. to 240° C. is preferable in which the cellulose stays at the solid content side, and the hemicellulose component and the lignin component have a sufficient decomposition speed.

The reaction pressure is preferably a pressure obtained by adding 0.1 to 0.5 MPa to the saturation vapor pressure of water at each of the reaction temperatures (180 to 240° C.) of the apparatus main body 13.

Furthermore, the reaction time is preferably 20 minutes or less, 3 to 10 minutes. This is because when the reaction is performed for a too long time, a rate of an excessively decomposed product increases, which is not preferable.

Examples of the biomass providing unit 12 that provides the biomass feedstock 11 from the normal pressure state to the pressurized state include means such as a screw, a piston pump, or a slurry pump.

Furthermore, although in the present embodiment, the hydrolysis apparatus is a vertical type apparatus, the present invention is not limited thereto, and the hydrolysis apparatus may be an inclined type hydrolysis apparatus having the gas-liquid interface 13a.

Here, the reason why the hydrolysis apparatus is the inclined type or the vertical type is that gas generated in the hydrolysis reaction, gas brought into the feedstock, and the like can be quickly released from the upper side, which is preferable. Moreover, since a decomposed product is extracted with the pressurized hot water 15, the concentration of an extract increases from the upper side to the lower side, which is preferable in terms of extraction efficiency.

Next, a saccharification/saccharide-concentrating apparatus 50 using the mixture slurry 24 to perform enzymatic saccharification and concentrate saccharide will be explained with reference to FIG. 3.

Figure 3:
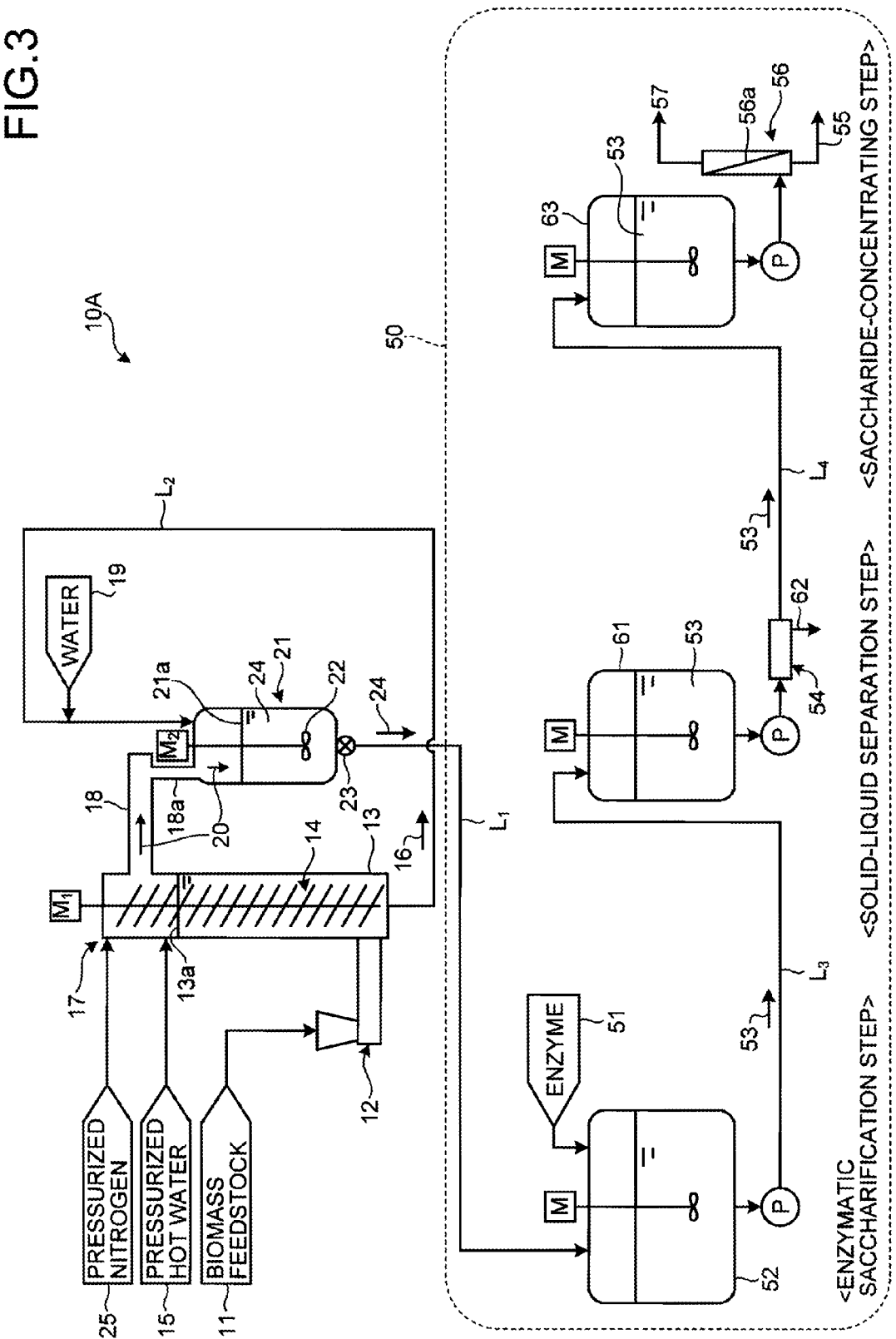
FIG. 3 is a schematic diagram of the biomass processing system according to the first embodiment.

As illustrated in FIG. 3, this saccharification/saccharide-concentrating apparatus 50 includes a saccharification tank 52 that subjects the mixture slurry 24 to enzymatic saccharification with an enzyme 51, a solid-liquid separation device 54 that separates a solid element from a saccharide solution 53 after the saccharification, and a moisture separation device 56 that is provided with a reverse osmosis (RO) membrane 56a and that removes water 57 from the saccharide solution 53 separated by the solid-liquid separation device 54 to obtain a concentrating saccharide solution 55.

The solid-liquid separation device 54 may use, for example, a screw decanter, a sand filtration device, an MF membrane, or the like alone or a combination thereof and thereby removes a solid material so that the RO membrane 56a can be protected. Further, in the prior stage side of the RO membrane 56a, an ultrafiltration membrane (UF membrane) is used to protect the RO membrane, and at the same time, enable recovery of an enzyme, so that the enzyme can be reused.

Furthermore, the moisture separation device 56 may use a loose RO membrane, a nanofiltration membrane (NF membrane), and the like.

Next, a procedure of processing steps of this saccharification/saccharide-concentrating apparatus 50 will be explained.

The mixture slurry 24 is a mixture of the biomass solid content 20 which is a hot water insoluble element that becomes hexose feedstock, and the discharge liquid 16 including a biomass hot-water soluble element that becomes pentose feedstock, and therefore, C6 saccharification and C5 saccharification proceed in the same line.

<Enzymatic Saccharification Step>

First, in the saccharification tank 52, the mixture slurry 24 is introduced via the discharge line L1, the enzyme 51 is added, and the saccharification with the enzyme reaction is performed in the enzymatic saccharification step.

<Solid-Liquid Separation Step>

Next, the saccharide solution 53 is stored in a first saccharide solution tank 61, subsequently, a solid residual liquid 62 such as lignin is separated by the solid-liquid separation device 54, and subsequently, the saccharide solution 53 is stored in a second saccharide solution tank 63. In the figure, reference characters $L_3$ and $L_4$ denote saccharide solution providing lines providing the saccharide solution 53.

<Saccharide-Concentrating Step>

Next, the water 57 is removed from the saccharide solution 53 by the moisture separation device 56 provided with the RO membrane 56a to obtain the concentrating saccharide solution 55.

This concentrating saccharide solution 55 is made into various kinds of organic feedstock in fermentation processing in a not-illustrated subsequent step.

In the present embodiment, the mixture slurry 24 is used to perform the saccharification, and therefore, saccharification at a low substrate concentration is provided, and high-speed saccharification becomes possible.

Furthermore, since slurry is used, agitation/transfer and the like can be performed with high operationality.

Furthermore, since the saccharification at a low substrate concentration is provided, the enzyme usage amount can be reduced.

Furthermore, the saccharide can be concentrated efficiently by the membrane processing using various kinds of membranes Furthermore, since the solid residual liquid 62 such as lignin thus separated has a high calorie, the solid residual liquid 62 can be used for fuel and the like. Furthermore, the solid residual liquid 62 such as lignin can be used for organic fertilizer application and chemical feedstock application (application as an adhesive agent of lignin and the like).

As described above, a saccharide solution production method using biomass feedstock of the present invention can efficiently produce a saccharide solution from biomass feedstock by providing the biomass feedstock 11 including cellulose, hemicellulose, and lignin from a normal pressure state to a pressurized state, subjecting the biomass feedstock 11 to hydrolysis by the hydrolysis processing unit 17 using the pressurized hot water 15, dissolving a lignin component and a hemicellulose component in the pressurized hot water 15, subsequently, charging the biomass solid content 20 discharged from the hydrolysis processing unit 17 into the slurrying vessel 21 which is in communication with the hydrolysis processing unit 17 and into which the discharge liquid 16 has been introduced, making the biomass solid content 20 into the mixture slurry 24, subjecting the mixture slurry 24 to enzymatic saccharification to obtain the saccharide solution 53, thereafter, separating a solid content, and then removing water, as illustrated in FIG. 2.

In the present embodiment, in the slurrying, the discharge liquid 16 is used, so that introduction of water from the outside can be eliminated, and therefore, the saccharification concentration can be increased, for example, from 1.5 wt % to 8 wt %. As a result, a saccharide solution concentrating device to be installed at a later stage side becomes unnecessary, or the size of the saccharide solution concentrating device can be reduced.

As described above, according to the present embodiment, the cellulose-based component and the hemicellulose component are decomposed in the solid-liquid contact state from the biomass feedstock, and thereafter, the biomass solid content which is a decomposed product thereof is charged into the liquid poured into the slurrying vessel 21 and thus subjected to the slurrying, and also the liquid sealing is made so that the effluence of pressurized gas can be prevented. This prevents the effluence of the gas for pressurization (for example, the pressurized nitrogen), and can greatly reduce the running cost.

As described above, according to the present embodiment, in the slurrying, the hot water discharge liquid is used without providing water from the outside, and therefore, the amount of consumption of water in the entire plant can be greatly reduced, and the cost can be reduced.

In addition, the saccharification is performed using the mixture slurry 24 in which the slurry biomass solid content that becomes hexose feedstock and the hot water discharge liquid that becomes pentose feedstock are mixed, and therefore, the saccharide concentration can be increased.

Furthermore, the saccharification is performed using the mixture slurry 24 in which the slurry biomass solid content that becomes hexose feedstock, and the hot water discharge liquid that becomes pentose feedstock are mixed, and therefore, the enzyme usage amount in the saccharification can be reduced, and the cost of enzyme usage can be reduced.

Furthermore, the saccharification is performed using the mixture slurry 24 in which the slurry biomass solid content that becomes hexose feedstock, and the hot water discharge liquid that becomes pentose feedstock are mixed, and therefore, the saccharification line can be a single line of one system, instead of two systems as in the related art, the enzymatic saccharification step becomes simple, and the equipment cost and the running cost can be reduced.

Furthermore, since the amount of consumption of water can be reduced, the amount of generation of waste liquid can be reduced, and the cost of disposal of the waste liquid can be reduced.

Second Embodiment

Next, another embodiment of a biomass processing system according to the present invention will be explained with reference to drawings. It is to be noted that the same members as those of the biomass processing system of the first embodiment are denoted with the same reference characters, and description thereof is omitted.

Figure 4:
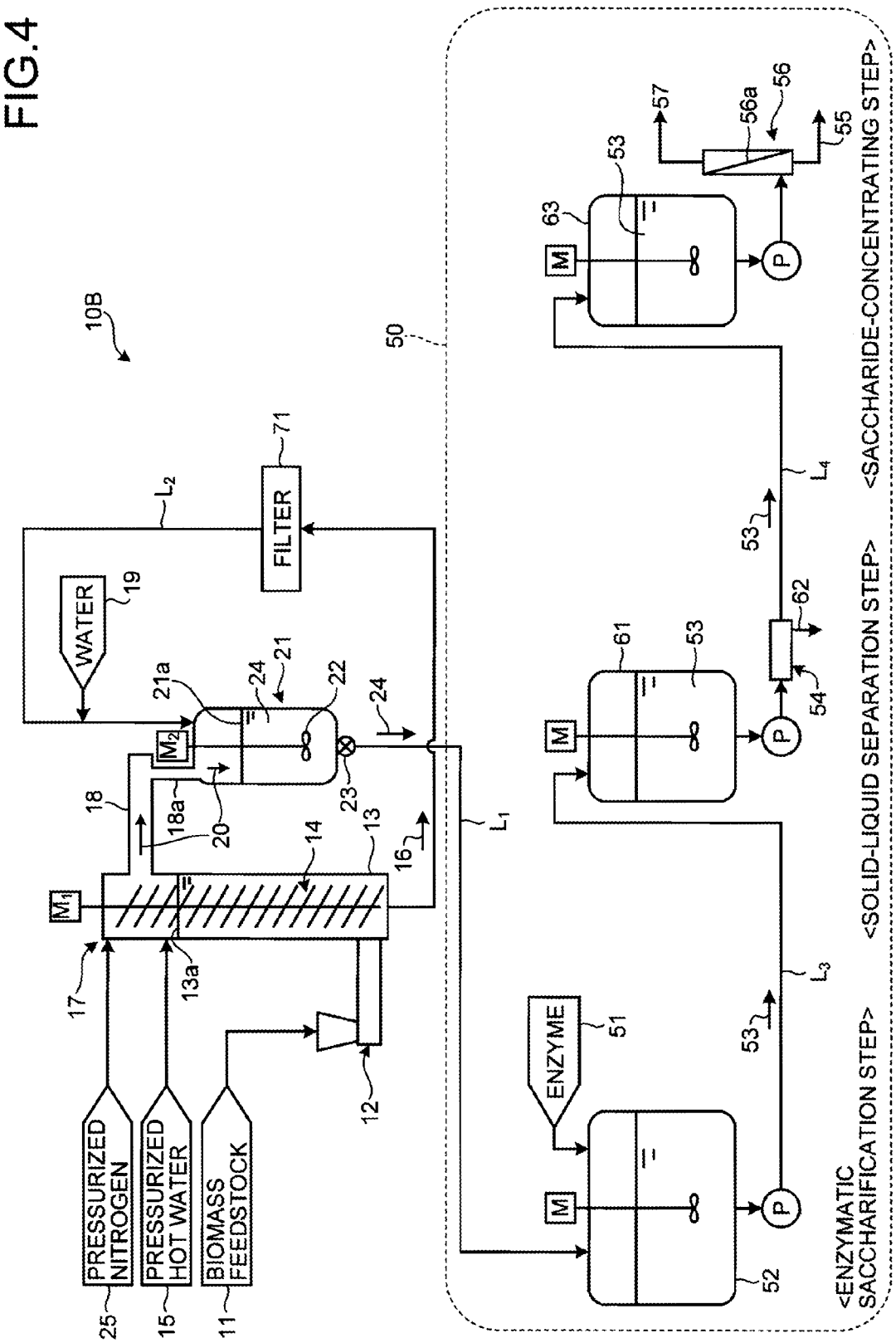
FIG. 4 is a schematic diagram of a biomass processing system according to a second embodiment.

FIG. 4 is a schematic diagram illustrating a biomass processing system according to a second embodiment.

As illustrated in FIG. 4, a biomass processing system 10B has a filter 71 provided in the hot water discharge liquid introducing line $L_2$ in the biomass processing system 10A of the first embodiment. This filter 71 is installed so that the solid content such as lignin in a discharge liquid 16 can be separated. This can prevent the saccharification inhibition caused by lignin.

Third Embodiment

Next, another embodiment of a biomass processing system according to the present invention will be explained with reference to drawings. It is noted that the same members as those of the biomass processing system of the first embodiment are denoted with the same reference characters, and description thereof is omitted.

Figure 5:
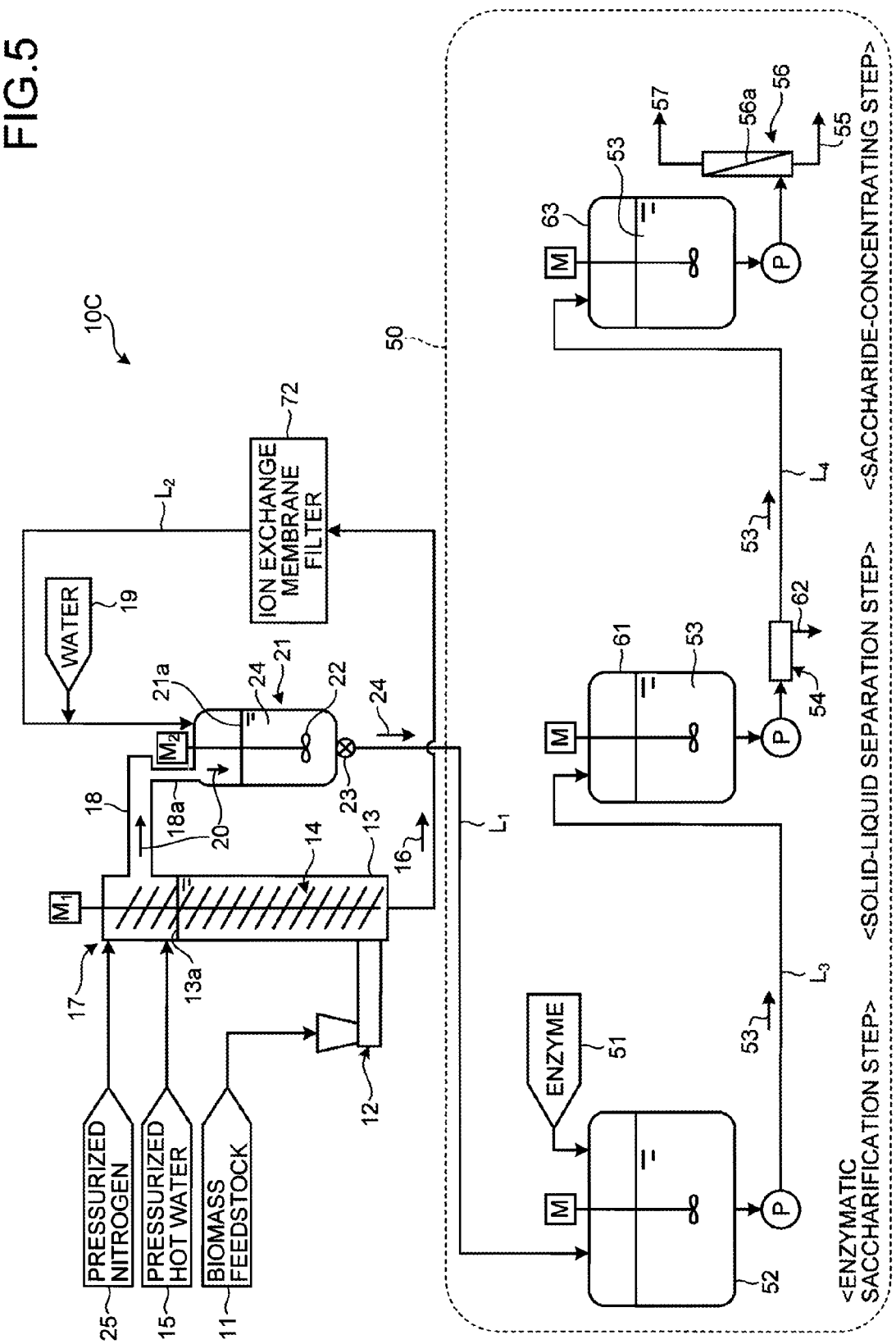
FIG. 5 is a schematic diagram of a biomass processing system according to a third embodiment.

FIG. 5 is a schematic diagram illustrating a biomass processing system according to a third embodiment.

As illustrated in FIG. 5, a biomass processing system 10C has an ion exchange membrane filter 72 provided in the discharge liquid line $L_2$ in the biomass processing system 10A of the first embodiment. This ion exchange membrane filter 72 is installed so that an acid substance dissolved in a discharge liquid 16 can be removed by the ion exchange. This can prevent the saccharification inhibition caused by an acid substance.

Fourth Embodiment

Next, another embodiment of a biomass processing system according to the present invention will be explained with reference to drawings. It is noted that the same members as those of the biomass processing system of the first embodiment are denoted with the same reference characters, and description thereof is omitted.

Figure 6:
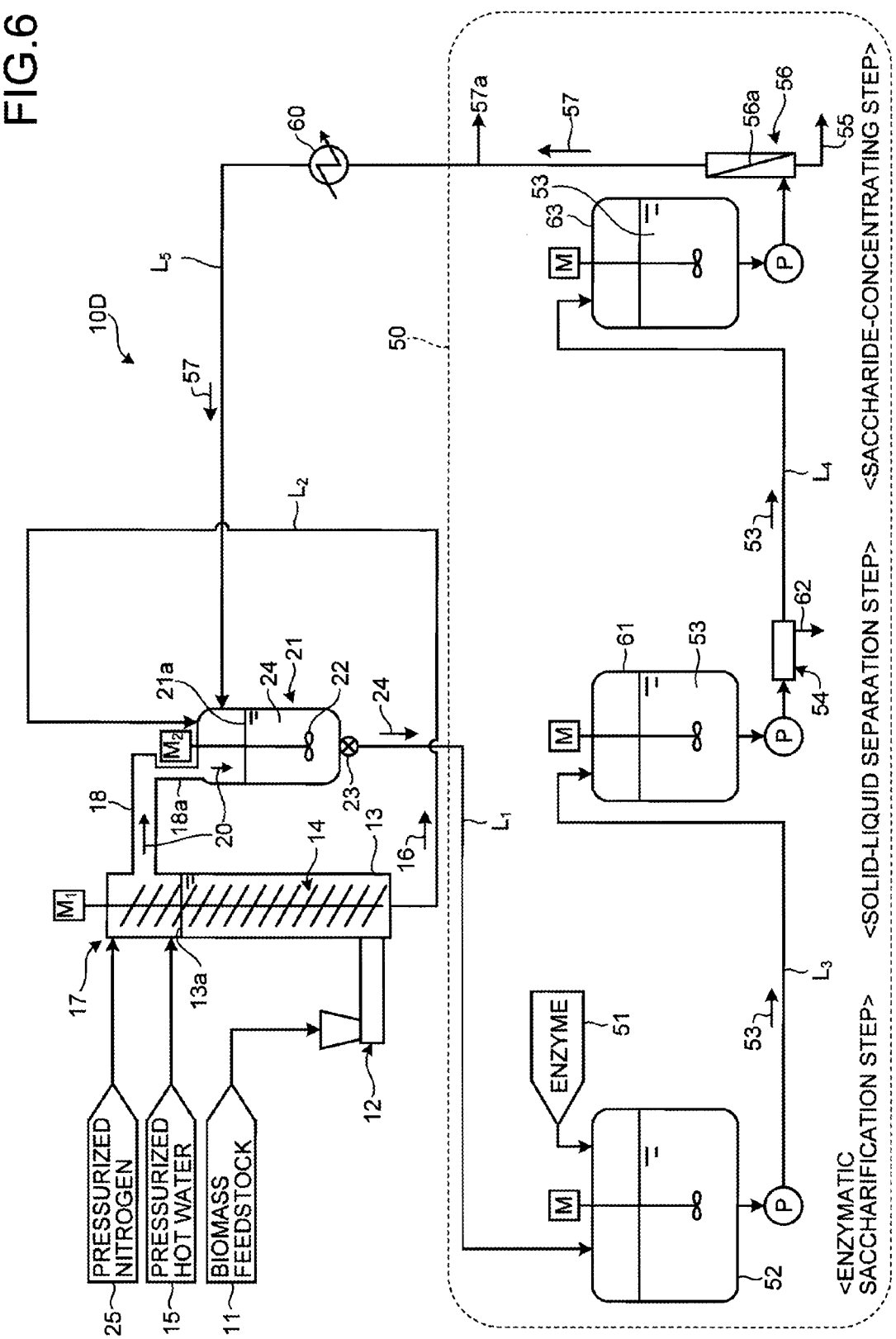
FIG. 6 is a schematic diagram of a biomass processing system according to a fourth embodiment.

FIG. 6 is a schematic diagram illustrating a biomass processing system according to a fourth embodiment.

As illustrated in FIG. 6, a biomass processing system 10D further has a water return line $L_5$ that returns water 57 separated from the moisture separation device 56 back to the slurrying vessel 21 in the biomass processing system 10C of the third embodiment.

Furthermore, in this water return line $L_5$, a cooling device 60 is interposed, so that after water 57 is cooled to a predetermined temperature, the water 57 can be returned back to the slurrying vessel 21.

Therefore, the separated water 57 can be reused, and stoppage of use or the reduced usage amount of water 19 to be provided to the slurrying vessel 21 can be achieved.

Fifth Embodiment

Next, another embodiment of a biomass processing system according to the present invention will be explained with reference to drawings. It is noted that the same members as those of the biomass processing system of the first embodiment are denoted with the same reference characters, and description thereof is omitted.

Figure 7:
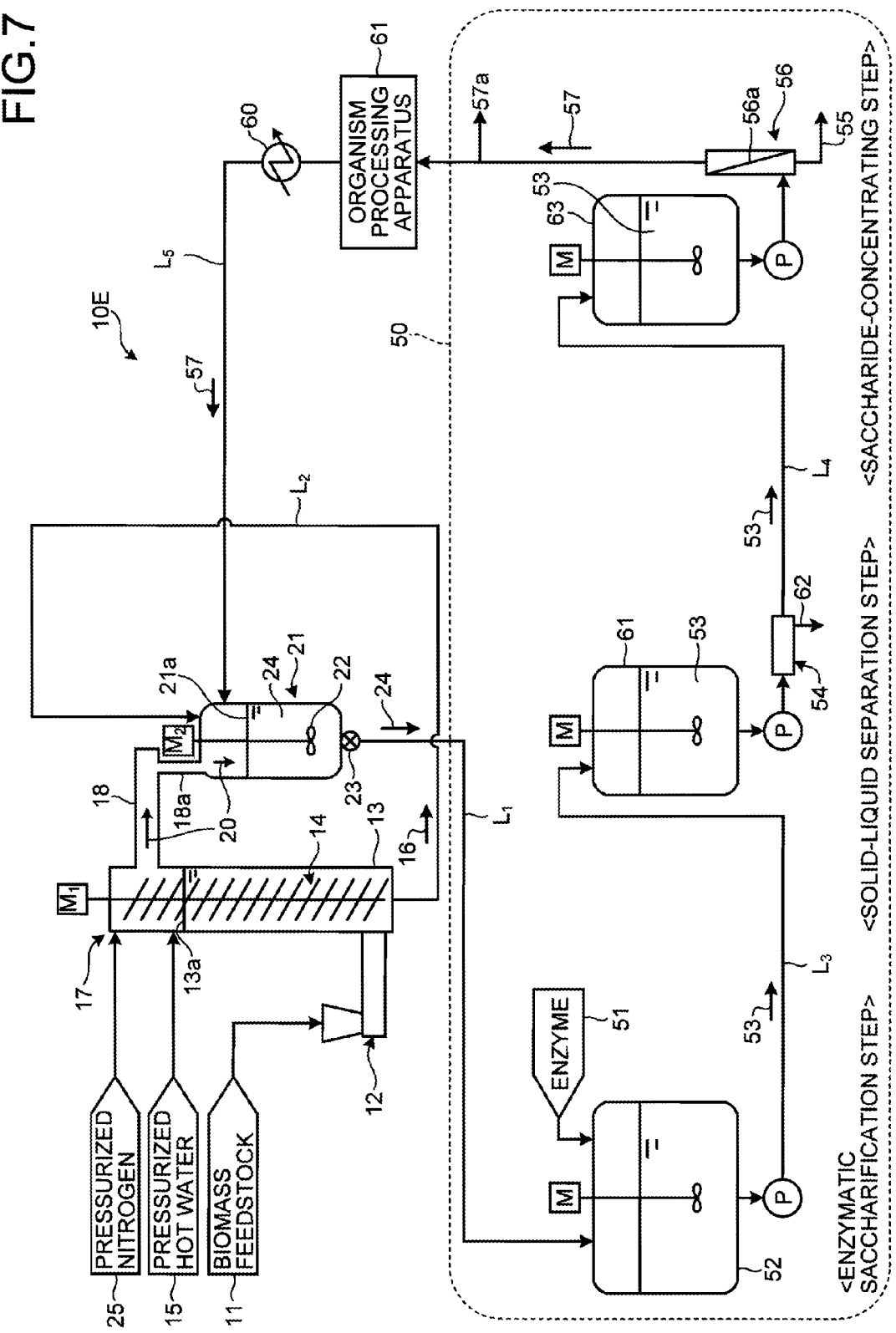
FIG. 7 is a schematic diagram of a biomass processing system according to a fifth embodiment.

FIG. 7 is a schematic diagram illustrating a biomass processing system according to a fifth embodiment.

As illustrated in FIG. 7, a biomass processing system 10E further has an organism processing apparatus 61 provided in the water return line $L_5$ in the biomass processing system 10D of the fourth embodiment, so that after water 57 is subjected to organism processing, the water 57 can be returned back to a slurrying vessel 21.

The water 57 separated by an RO membrane 56a in a saccharide-concentrating step includes a reaction inhibition substance (low molecule organic compound), and therefore, the water 57 can be easily processed by the organism processing apparatus 61. Then, for example, a methane fermentation organism processing apparatus is used as the organism processing apparatus to recover methane, and the methane can be utilized for fuel and the like.

As described above, according to the biomass processing system of the present invention, a cellulose-based component and a hemicellulose component are decomposed in a high-temperature/high-pressure condition from biomass feedstock, and thereafter, a biomass solid content which is a decomposed product thereof is charged into a liquid into which a discharge liquid 16 provided inside the slurrying vessel is introduced, and thus subjected to slurrying, and also the liquid sealing is made so that the effluence of pressurized gas can be prevented. This prevents the effluence of gas for pressurization (for example, pressurized nitrogen), and can greatly reduce the running cost.

Furthermore, a biomass solid material is made into slurry with the discharge liquid 16 to be made into mixture slurry 24, and thus makes handling thereof easy and becomes more suitable for a subsequent saccharification step, so that the saccharide solution can be produced efficiently. Furthermore, based on this saccharide solution, various kinds of organic feedstock (for example, alcohols, substitutes for petroleum, or amino acids) can be produced efficiently. Furthermore, based on this saccharide solution, various kinds of organic feedstock (for example, alcohols, substitutes for petroleum, or amino acids) can be produced efficiently, such as LPG, automobile fuel, aircraft jet fuel, kerosene, diesel oil, various kinds of heavy oils, fuel gas, naphtha, ethylene glycol which is a naphtha decomposed product, lactic acid, alcohol (such as ethanol), amine, alcohol ethoxylates, vinyl chloride polymers, alkyl aluminum, PVA, vinyl acetate emulsion, polystyrene, polyethylene, polypropylene, polycarbonate, MMA resins, nylon, and polyester. Therefore, the biomass-derived saccharide solution can be efficiently utilized as a substitute for a chemical product derived from petroleum which is exhaustible fuel and as the material for producing such a substitute.

Further, since the biomass solid content is charged into the liquid, the reaction can be stopped efficiently by cooling the biomass solid content by means of direct heat exchange using the liquid, and in addition, since an acid and an alkali are diluted, excessive decomposition of the remaining hemicellulose, the remaining lignin, and the main component cellulose accompanied by the biomass solid content can be suppressed. As a result, generation of a reaction inhibition component can be suppressed, and in addition, the recovery rate of the cellulose component can be improved.

REFERENCE SIGNS LIST 10A to 10E BIOMASS PROCESSING SYSTEM
11 BIOMASS FEEDSTOCK
12 BIOMASS PROVIDING UNIT
13 APPARATUS MAIN BODY
14 FIRST SCREW MEANS
15 PRESSURIZED HOT WATER
16 HOT WATER DISCHARGE LIQUID
17 HYDROLYSIS PROCESSING UNIT
18 BIOMASS SOLID CONTENT DISCHARGE UNIT
19 WATER
20 BIOMASS SOLID CONTENT
21 SLURRYING VESSEL
22 AGITATION MEANS
23 DISCHARGE UNIT
24 MIXTURE SLURRY
25 PRESSURIZED NITROGEN
50 SACCHARIFICATION/SACCHARIDE-CONCENTRATING APPARATUS

The invention claimed is:
1. A biomass processing system comprising:
a hydrolysis processing unit that provides a first gas-liquid interface therein and comprises:
  a biomass providing unit that supplies biomass feedstock containing cellulose, hemicellulose, and lignin;
  a supply inlet that supplies pressurized hot water;
  an apparatus main body that brings the biomass feedstock and the pressurized hot water into countercurrent contact so as to hydrolyze the biomass feedstock;
  an outlet from which a hot water discharge liquid containing a biomass hot-water soluble element dissolved in the pressurized hot water is discharged; and
  a biomass solid content outlet from which a biomass solid content is discharged, the biomass solid content containing a hot water insoluble element of the biomass feedstock;
a biomass solid content discharge unit that discharges the biomass solid content processed by the hydrolysis processing unit;
a slurrying vessel that is in communication with the biomass solid content discharge unit and that subjects the discharged biomass solid content to slurrying; and
a discharge liquid introducing line that introduces, into the slurrying vessel, the hot water discharge liquid contain- ing the biomass hot-water soluble element discharged from the hydrolysis processing unit, wherein the biomass solid content is mixed with the hot water discharge liquid to be made into a mixture slurry, wherein a filter that separates a solid content including a lignin component from the hot water discharge liquid is interposed in the discharge liquid introducing line, wherein the biomass processing system further comprises:

a saccharide-concentrating apparatus that is provided downstream of the slurrying vessel, that performs enzymatic saccharification on the mixture slurry to produce a saccharide solution, and that separates water from the saccharide solution so as to concentrate the saccharide solution;

a water return line that returns the water to the slurrying vessel; and an organism processing apparatus that is provided in the water return line and that performs organism processing on a reaction inhibition substance in the water.

2. The biomass processing system according to claim 1, wherein an ion exchange membrane filter that removes an acid substance dissolved in the hot water discharge liquid from the hot water discharge liquid by ion exchange is interposed in the discharge liquid introducing line.

3. The biomass processing system according to claim 1, wherein cooling means is interposed in the discharge liquid introducing line.

4. The biomass processing system according to claim 1, wherein the saccharide-concentrating apparatus comprises a saccharification tank that saccharifies the mixture slurry subjected to the slurrying in the slurrying vessel.

5. The biomass processing system according to claim 4, wherein the saccharide-concentrating apparatus comprises:

a solid-liquid separation device that separates a solid element from a saccharide solution saccharified by the saccharification tank; and a moisture separation device that removes water from the saccharide solution from which the solid element has been separated.

6. A saccharide solution production method using biomass feedstock, comprising:

providing the biomass feedstock including cellulose, hemicellulose, and lignin from a normal pressure state to a pressurized state, and performing hydrolysis processing by a hydrolysis processing unit on the biomass feedstock under a high-temperature/high-pressure condition; and subsequently, charging a biomass solid content discharged from the biomass processing unit into a slurrying vessel into which water has been poured and which is in communication with the biomass processing unit, and making the biomass solid content into a slurry biomass solid content;

subjecting the slurry biomass solid content to enzymatic saccharification to obtain a saccharide solution, thereafter separating a solid content, and then removing water, wherein the saccharide solution production method further comprises:

separating a solid content including a lignin component from a hot water discharge liquid, the hot water discharge liquid including a biomass hot-water soluble element discharged from the hydrolysis processing unit;

introducing the hot water discharge liquid into the slurrying vessel and subjecting to slurrying to be made into a mixture slurry, the solid content including the lignin component having been separated from the hot water discharge liquid;

performing the enzymatic saccharification on the mixture slurry to produce a saccharide solution, and separating water from the saccharide solution so as to concentrate the saccharide solution; and performing organism processing on a reaction inhibition substance in the water and returning the water to the slurring vessel.

7. The saccharide solution production method using biomass feedstock according to claim 6, further comprising:

prior to the step of introducing the hot water discharge liquid, removing an acid substance dissolved in the hot water discharge liquid from the hot water discharge liquid by an ion exchange.

\* \* \* \* \*